United States Patent
Fenton et al.

(10) Patent No.: US 8,412,537 B1
(45) Date of Patent: Apr. 2, 2013

(54) SYSTEM AND METHOD FOR EPISODE SERVICE ITEM COST ESTIMATION BASED ON HISTORICAL DATA

(75) Inventors: Stefanie H. Fenton, Redwood City, CA (US); Suzanne Y. Pellican, Menlo Park, CA (US); Daniel W. Beck, San Francisco, CA (US)

(73) Assignee: Intuit Inc., Mountain View, CA (US)

( * ) Notice: Subject to any disclaimer, the term of this patent is extended or adjusted under 35 U.S.C. 154(b) by 1019 days.

(21) Appl. No.: 11/955,066

(22) Filed: Dec. 12, 2007

(51) Int. Cl.
*G06Q 10/00* (2006.01)
*G06Q 50/00* (2006.01)
*G06Q 40/00* (2006.01)

(52) U.S. Cl. ..................................... 705/2; 705/3; 705/4
(58) Field of Classification Search ........................ None
See application file for complete search history.

(56) References Cited

U.S. PATENT DOCUMENTS

| | | | |
|---|---|---|---|
| 5,924,074 A | 7/1999 | Evans | |
| 6,032,119 A | 2/2000 | Brown | |
| 6,879,959 B1 | 4/2005 | Chapman | |
| 6,988,075 B1 | 1/2006 | Hacker | |
| 7,165,062 B2 | 1/2007 | O' Rourke | |
| 7,234,064 B2 | 6/2007 | Menschik | |
| 7,249,040 B1 | 7/2007 | Binns | |
| 2003/0074329 A1 | 4/2003 | Bruno | |
| 2003/0110141 A1 | 6/2003 | Boutault | |
| 2004/0039710 A1* | 2/2004 | McMillan et al. | 705/400 |
| 2006/0242089 A1 | 10/2006 | Vahidi | |
| 2007/0043595 A1* | 2/2007 | Pederson | 705/2 |
| 2007/0106533 A1* | 5/2007 | Greene | 705/2 |
| 2007/0244714 A1* | 10/2007 | McCluskey et al. | 705/2 |
| 2007/0271203 A1 | 11/2007 | Delvat | |
| 2007/0282664 A1 | 12/2007 | Monster | |
| 2007/0299698 A1* | 12/2007 | Anandarao et al. | 705/4 |

\* cited by examiner

*Primary Examiner* — Robert Morgan
*Assistant Examiner* — Eliza Lam
(74) *Attorney, Agent, or Firm* — McKay and Hodgson, LLP; Philip McKay; Sean P. Lewis

(57) ABSTRACT

A system is implemented to collect data from a plurality of different sources. The data comprises information about episodes experienced by a plurality of consumers. The system is configured to receive a cost estimate request from a user for a specified episode. The may access the data to determine a plurality of service items for the specified episode and the associated cost of each service item. An episode may be associated with one or many service items. The network-based service may generate a response to the cost estimate request. The response may include the plurality of service items determined for the specified episode and the associated cost information. The system may send the response to the user.

18 Claims, 9 Drawing Sheets

Healthcare Estimation Application                                    _ □ ×

640                    650
← → ↺

Gallbladder Removal Using Scope    Your Custom           Estimated Paid By Your Health Plan $4,152
Dr. Smith & His Anesthesiologist   Out-Of-Pocket Estimate  Estimated Billed By Your Provider(s) $7,004
                                   $2,852

| Service Details | Provider | Qty | Out Of Pocket Estimate | In-Network You Could Save |
|---|---|---|---|---|
| Diagnosis | | | | |
| Tissue Test | In Network Lab | 2 | $78 | $0 |
| Chest X-Ray | In Network Facility | 1 | $4 | $0 |
| Treatment & Procedures | | | | |
| Anesthesiologist, Stomach | Dr. John Doe | 1 | $1,918 | $343 |
| Surgeon, Gallbladder Remova | Dr. Bob Smith | 1 | $741 | $667 |
| Follow-Up Care | | | | |
| Follow-Up Office Visit | Dr. John Doe | 1 | $61 | $51 |
| | | Totals | $2,852 | $1,061 |

610 — Diagnosis
620 — Treatment & Procedures
630 — Follow-Up Care
660 — Totals

FIG. 6

SYSTEM AND METHOD FOR EPISODE SERVICE ITEM COST ESTIMATION BASED ON HISTORICAL DATA

BACKGROUND

When healthcare consumers are confronted with a new health condition, they frequently have difficulty understanding what treatments to expect, what healthcare costs to expect, what healthcare provider choices they may have, and what treatments are covered under their health plan. An individual receiving a new diagnosis may be uncertain as to what they can expect both from a treatment and financial standpoint.

In addition, when a healthcare consumer is facing a single treatment or treatment regimen that requires more than a simple office visit, often the healthcare consumer's primary care physician makes healthcare choices for the consumer based on professional relationships the physician has with facilities (e.g., hospitals) and colleagues. This selection process does not give the healthcare consumer visibility into options he or she may have regarding the selection of healthcare providers and further does not give the consumer the opportunity to perform healthcare provider comparisons.

Further, healthcare providers may not advertise the costs of their services (e.g., the cost of a visit or a treatment). This may make it difficult for healthcare consumers to understand treatment costs, which may be particularly important for healthcare consumers that do not have health insurance.

Generally speaking, healthcare consumers rarely have a good understanding of healthcare options and treatment costs prior to undergoing treatment.

SUMMARY

Various embodiments of a method and system for episode service item cost estimation based on historical data are disclosed for estimating service item costs and service provider options. The term "service item", as used herein, may refer to any product or service provided by a service provider. In some healthcare related embodiments, a service item may be analogous to a treatment item. The system may collect data about episodes, each experienced by a respective plurality of consumers.

In some embodiments, data collected from various entities may include the types of service items received by consumers. Collected data may include service item costs and the costs covered by various insurance plans. Information about a service items may include a date and/or time the service item was received, the provider of the service and/or the facility where the service item was received, and the cost of the service item.

In some embodiments, the system may receive a cost estimate request from a user for a specified episode. (An episode may be defined as a condition requiring one or more service items over time.) The system may access data to analyze a plurality of service items for the specified episode and determine cost information for each determined service item.

The system may generate a response to the cost estimate request made by the user. The response may indicate the plurality of service items determined for the specified episode and the associated cost information for each service item. The system may send the response to the user.

In some embodiments, the response sent to the user may include insurance plan information and cost information determined according to the insurance plan information. In addition, the response sent to the user may include healthcare provider comparative cost information. This information may be beneficial to the users, for example, to shed light on all the treatments and medications they can expect with certain health conditions. The information may enable the user who receives a diagnosis to understand what they can expect throughout the course of treating their health condition. The information may help users select healthcare providers and may provide users with a range of approximate costs for the treatments and medications they can expect to receive. In some embodiments, the user may want to view all treatments associated with a health episode (e.g., including all treatments for diagnosis, procedures and recovery). In other embodiments, the user may want to view just the treatments associated with a specific surgery or specific recovery from an injury.

In some embodiments, response information may be generated, sent to the user and displayed on a results screen (e.g., within a web browser) as a result of the request (e.g., requested by the user). In some embodiments, the information generated may include the name of the health condition, treatment descriptions and costs, medications, recovery therapy, etc. In some embodiments, several detailed treatment items associated with a single health episode may be generated and sent to the user. Summary information may be generated and sent to the user. In some embodiments information may be generated related to two or more healthcare providers that treat the same health condition so that comparisons can be made.

BRIEF DESCRIPTION OF THE DRAWINGS

FIG. 6 is a user interface diagram, illustrating the display of treatment options and treatment costs related to a health condition, according to an embodiment.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words, "include", "including", and "includes" mean including, but not limiting to.

DETAILED DESCRIPTION OF EMBODIMENTS

Figure 1:
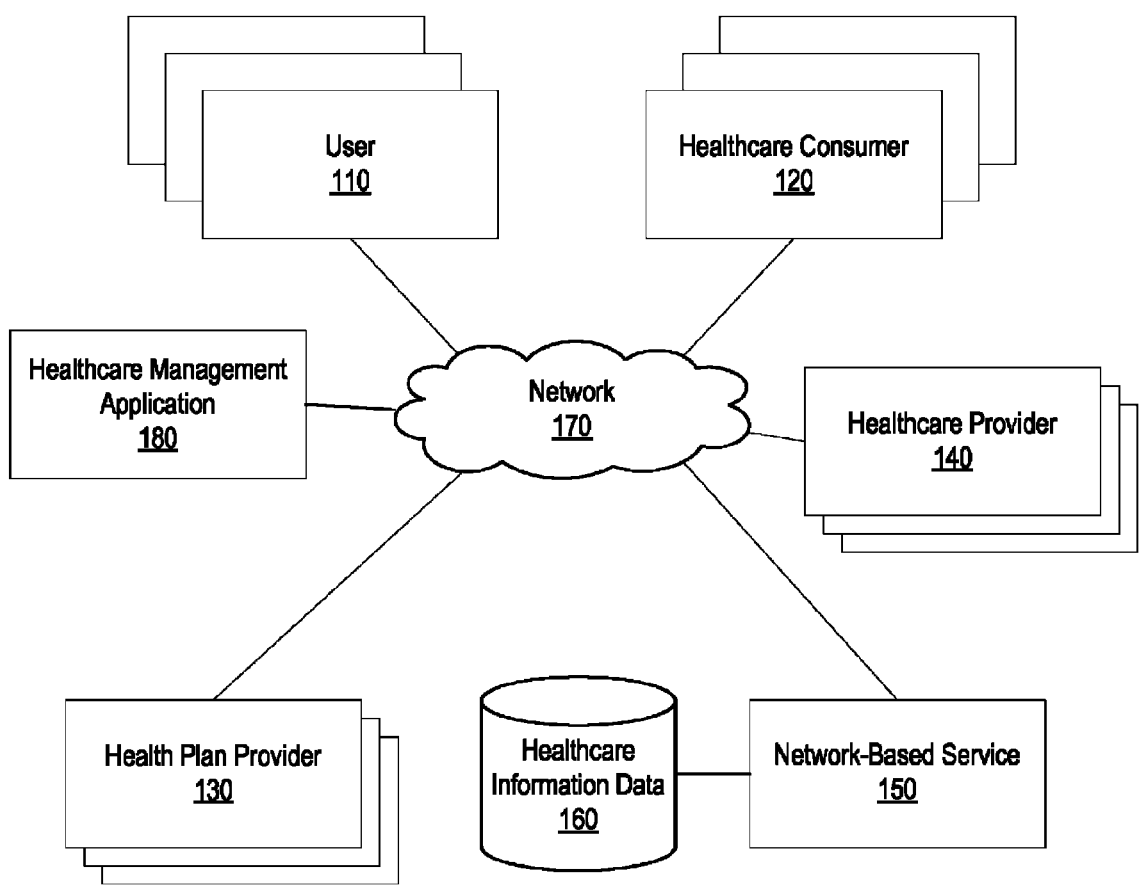
FIG. 1 is a block diagram illustrating a system for healthcare treatment estimating, according to an embodiment.

FIG. 1 is a block diagram illustrating a system for healthcare treatment estimating, according to an embodiment. It should be noted that in various embodiments of the methods described below, one or more of the elements described may be performed concurrently, in a different order than shown, or may be omitted entirely. Other additional elements may also be performed as desired.

Various embodiments of a network-based service 150 may collect healthcare information data 160 from a plurality of sources (e.g., healthcare providers 140 and health plan providers 130) for various healthcare consumers 120. The network-based service 150 may analyze the information and use the healthcare information data 160 to provide information in an organized form to one or more users 110. As used herein, "user" includes users 110 of the network-based service. Users 110 may or may not be healthcare consumers 120 who may also be sources of the healthcare information data 160.

In some embodiments, the network-based service 150 may provide users 110 (e.g., through a search interface) with information about health episodes and their related treatments, medications, costs, etc. The information may be used, for example, to determine healthcare estimates or "What-if" scenarios related to a health episode. The healthcare estimates may help the user understand the plurality of detailed treatments and medications typically administered for a specified health episode. Healthcare estimates (e.g., generated responses to cost estimate requests) may be tailored to include different providers, treatments or health plan options. The generated response of each cost estimate request may be returned to a user so that the user may compare the healthcare estimates.

The generated response is referred to as a cost estimate because the response is generated according to previous healthcare information received from a plurality of sources; however, the generated response is not necessarily indicative of the exact current or future treatment costs or treatment regimens. Further, every healthcare consumer is different and healthcare providers may tailor treatments and medications according to each healthcare consumer's unique situation.

In some embodiments, the information returned by network-based service 150 may provide users 110 with information to help them negotiate with healthcare providers 140 and health plan providers 130. Health information for a specific region (e.g., specific to a certain zip code) may be provided to allow users 110 to view treatment items, procedures and medications (and, for example, their related costs) in their region.

Although network-based service 150 is illustrated in FIG. 1 as a single system, in various embodiments network-based service 150 may be implemented as a distributed system, such that many different systems, services, data sources and applications may be utilized to provide the functionality described herein as network-based service 150. These systems may be located in one physical location or in different physical locations, configured to communicate with one another via a network 170.

Healthcare information data 160 may include healthcare related information collected about health conditions, each experienced by a respective plurality of healthcare consumers 120. Collecting healthcare information data 160 may include aggregating healthcare information for several respective pluralities of healthcare consumers 120 (corresponding to their respective health conditions) into one data set.

In some embodiments, the healthcare-related information 160 may include information about the treatments and medications experienced by healthcare consumers 120 during specific health episodes. The healthcare information data 160 may include aggregate information and/or treatment item detail information related to the specific health episodes experienced by a plurality of healthcare consumers 120. This information may also include healthcare provider 140 information, health plan provider information 130, health plans, procedure, treatment and diagnostic codes, medication costs, costs covered by various health plans, etc. More detailed information may be collected with respect to specific treatments and medications experienced by healthcare consumers 120. Information collected for a treatment may include a date and/or time of the treatment, the healthcare provider 140 for the treatment (e.g., the name of the physician performing the treatment and/or the facility where the treatment was performed), the cost of the treatment, a treatment recipient's health plan and the amount covered by the health plan along with an actual cost to the recipient, etc.

In some embodiments, information about a cost the healthcare consumer 120 was able to negotiate from the healthcare provider 140 may be collected. Other information about the treatment is also contemplated. For example, the healthcare consumer 120 may provide the system a quality rating (e.g., a rating that provides a healthcare consumer's assessment of the quality of the treatment, follow-up, etc.). Other information may include the medication taken before, during, and after the treatment, the healthcare consumer's zip code, and the zip code of the facility where the treatment was administered. Other geographic segment identifiers may also be used (e.g., area codes). Information may be collected for similar treatments (e.g., performed on different healthcare consumers 120 by different healthcare providers 140, etc.). Information may include symptoms (e.g., symptoms experienced by a healthcare consumer 120 with the health condition).

In some embodiments network based service 150 may be part of a healthcare management application. The healthcare information data 160 may be collected by the healthcare management application 180 used by several users 110, healthcare consumers, 120, health plan providers 130 and healthcare providers 140. Healthcare information data 160 may be entered by individuals (e.g., healthcare consumers 120 and/or users 110), healthcare providers 140 (e.g., physicians, hospitals, health clinics, etc.), health plan providers 130 (e.g., insurance companies) and other sources. In some embodiments healthcare consumers 120 may include users 110 (and vice-versa).

In some embodiments, healthcare information data 160 may be collected by a healthcare management application 180. The healthcare management application 180 may send healthcare information data 160 to network-based service 150. In other embodiments, network-based service 150 may retrieve healthcare information data 160 from the healthcare management application 180. In other embodiments, network-based service 150 may be a component of a healthcare management application 180. The healthcare management application 180 may, in some embodiments, provide the healthcare consumer 120 with a framework and tools for collecting, organizing, and managing information related to their health history; past, current and future health services; health insurance plan(s) (e.g., what services are covered, coverage limits, claim status, and explanations of benefits); and finances related to healthcare (e.g., health insurance premiums, deductibles, co-payments, benefit payments, reimbursements from Flexible Spending Accounts (FSAs), Health Reimbursement Accounts (HRAs), health savings accounts, maximum out-of-pocket expenses, and maximum lifetime benefits). In some embodiments, the healthcare management application 180 may be configured to provide a healthcare consumer 120 with a comprehensive and detailed health history, or may allow the healthcare consumer 120 to extract and/or analyze his or her information regarding a particular health condition or event (e.g., an injury or illness) or a particular healthcare-related service (e.g., a particular diagnostic exam or a course of treatment for a chronic condition).

In some embodiments, the healthcare management application 180 may be implemented as a web-based service to which healthcare consumers 120, and/or employers may subscribe. The healthcare management application may be implemented as a stand-alone application, such as one installed and executed on a desktop computer by a user 110. A healthcare management application 180 may include both a locally installed application (i.e., a client portion) and a remote, web-based application (i.e., a server portion). For example, in one embodiment, a healthcare consumer 120 may enter healthcare-related information on a locally installed client application and then may upload the information to a healthcare management application 180 server for secure storage and/or further analysis.

In various embodiments, the healthcare management application 180 may receive information from one or more of: healthcare consumers 120, healthcare providers 140, health plan providers 130 (e.g., health insurance representatives), and financial institutions or other sources. The information received and/or managed by the healthcare management application 180 may be formatted according to a standard information exchange format. The healthcare management application 180 may in some instances maintain the healthcare-related information 160 in one or more databases (or in other suitable formats) in local or remote storage, or in a combination of the two. For example, a database located on a healthcare management application 180 server may be configured to securely store healthcare-related information 160 for multiple individual healthcare consumers 120 or for employees of one or more corporations subscribing to a healthcare management service, while a database stored locally on a system user's computing system may include only his or her own personal health information.

Network 170 may be configured to allow data to be exchanged between network-based service 150 and other computing systems attached to network 170, such as user 110. Network 170 may correspond to various methods of communication between a user and an entity and may include, but are not limited to communication via Hypertext Transfer Protocol (HTTP), Simple Object Access Protocol (SOAP), Remote Method Invocation (RMI), web service communication and application server communication. In some cases, network 170 may represent communication via telephone, fax, email, real-time messages (e.g., instant messages), text messages, voice messages, and electronic documents (e.g., email attachments or file transfers). In general, network 170 may include any method that two entities may utilize to communicate with each other. While network 170 may be illustrated in a generalized manner, one of ordinary skill in the art will recognize that network 170 is meant to be representative of a complete communication path between network-based service 150 and user 110 in accordance with the specific type of communication channel. For example, network 170 may represent an email communication channel including various intermediate destinations and/or systems such as email clients, email servers, and/or communication networks (e.g., the Internet). In another example, a communications channel may include one or more telecommunications networks as well as various network devices including circuits, switches, routers and/or gateways. In other embodiments, network 170 may allow data to be exchanged between nodes of network-based service 170. In various embodiments, network 170 may support communication via wired or wireless general data networks, such as any suitable type of network, such as the public Internet and/or an Ethernet LAN; via telecommunications/telephony networks such as analog voice networks or digital fiber communications networks; via storage area networks such as Fibre Channel SANs, or via any other suitable type of network and/or protocol.

Figure 2A:
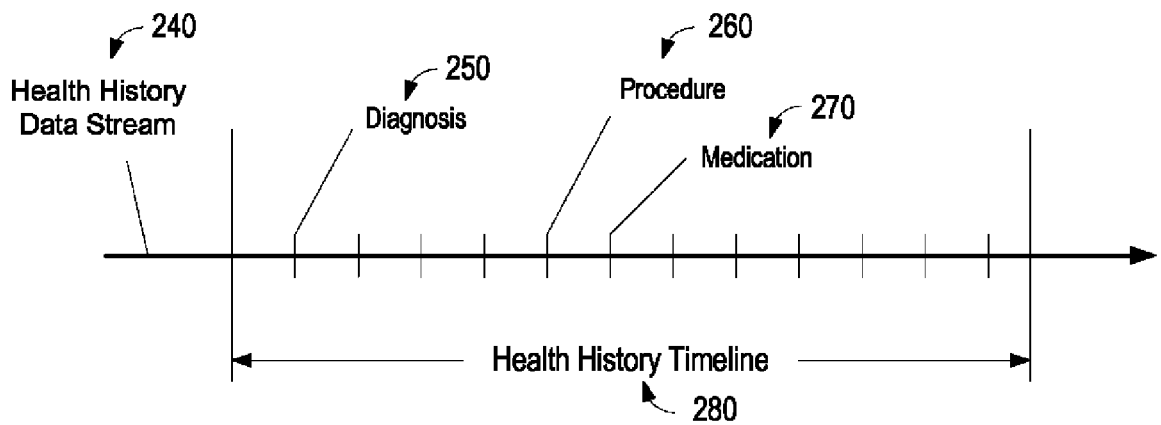
FIG. 2A is a line diagram illustrating a health history data stream, according to an embodiment.

FIG. 2A illustrates a health history timeline, including milestones for a patient's diagnosis and treatment. The health history timeline 280 illustrates how a health history data stream 240 may be generated over time. The data generated at each milestone indicated on health data stream 240 may be collected by network-based service 150 and stored in healthcare information data 160.

Typically, a healthcare consumer 120 experiences one or more symptoms that cause him or her to visit a healthcare professional. The healthcare professional may diagnose the healthcare consumer 120 with an illness or a condition as shown at item 250. The diagnosis may lead the healthcare professional to schedule a medical procedure, as shown at item 260. (e.g., X-Ray or blood test.) After the procedure, the healthcare professional may prescribe a medication for the healthcare consumer 120 as shown at item 270. (FIG. 2A is provided as an example and many variations are possible.)

Each healthcare consumer 120 that interacts with a healthcare professional along the health history timeline 280 may generate one or more data elements, collected by network-based service 150 and stored in healthcare information 160. These data elements may include health condition information, healthcare claim information, healthcare consumer billing information and many other elements. In addition, if the healthcare consumer 120 has health insurance, health plan information may also be generated and collected. This data may be collected as healthcare providers 140, health plan providers 130 and healthcare consumers 120 interact with a healthcare management application 180. As treatments are administered, the health care providers 140, health plan providers 130 and the healthcare consumer 120 themselves may enter information into the healthcare management application 180. Network-based service 150 may either retrieve this information from the healthcare management application or receive the information from the healthcare management application. For example, the healthcare management application may receive claim information or explanation of benefits information from health plan provider 130 and/or consumer 120. Similarly, the healthcare management application may receive billing and/or payment information from healthcare consumers 120, health plan providers 130 and healthcare providers 140.

Figure 2B:
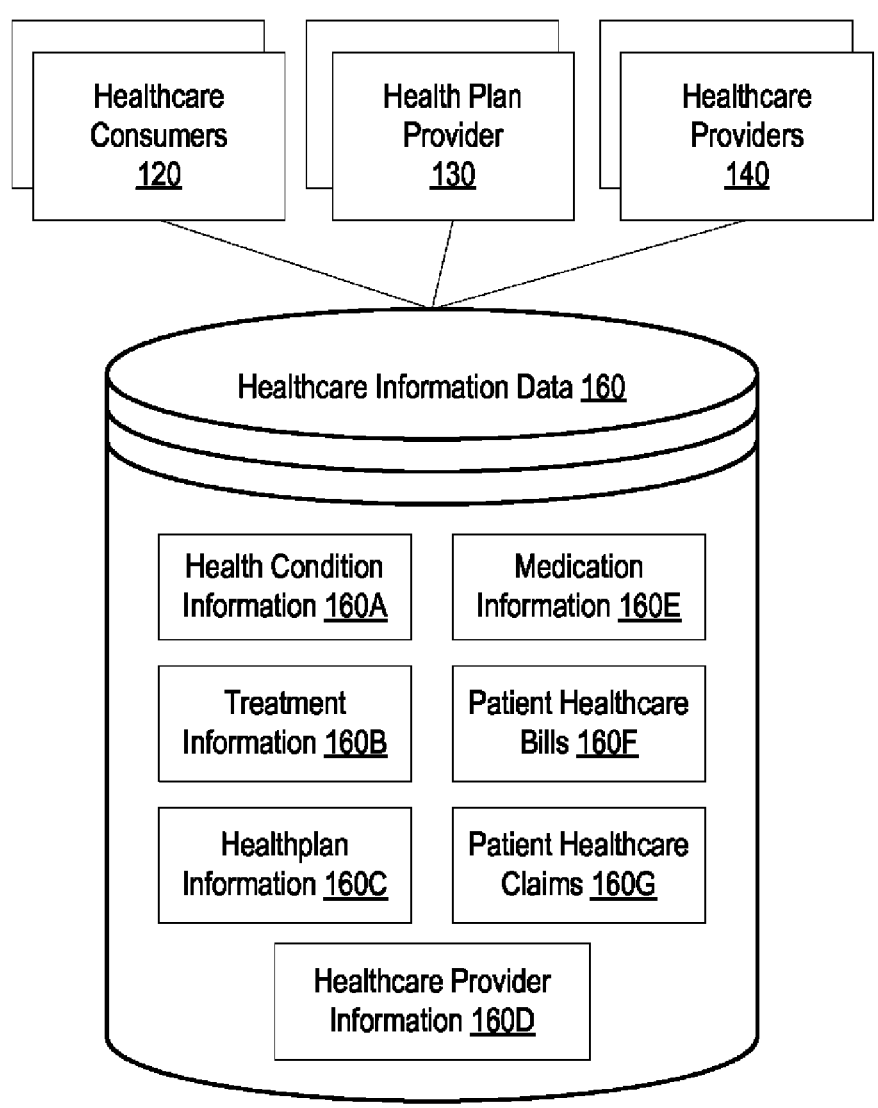
FIG. 2B is a block diagram illustrating healthcare information, according to an embodiment.

FIG. 2B is a diagram illustrating healthcare information data 160, according to an embodiment. The network-based service 150 may collect information from one or more of: healthcare consumer 120, health plan providers 130 (e.g., health insurance representatives) and healthcare providers 140 (e.g., physicians). The network-based service 150 may collect health information 160, for example as shown in health history data streams 240.

In some embodiments, health condition information 160A may include information about a healthcare consumer's 120 specific health condition, including diagnosis (e.g., broken ankle or arthritis), the healthcare provider 140 (e.g., physician) that made the diagnosis, the date and time the diagnosis was made and the facility where the diagnosis was made. One healthcare consumer 120 may have one or many health conditions 160A. Treatment information 160B may include one or more treatments administered to a healthcare consumer 120. Examples include blood tests, surgery and X-Rays. Many other treatment options have been contemplated. Health plan information 160C may include information about a healthcare consumer's insurance coverage. This information may include coverage limits, in-network and out-of-network costs, information about what was or was not covered regarding a healthcare consumer's specific treatments and medications. Healthcare provider information 160D may include information about the healthcare providers 140 a healthcare consumer 120 may have used for specific diagnosis and treatment related to a health condition. Healthcare provider information 160D may include the provider's name, address and specialty. Patient healthcare claim information 160G may include health plan claim information related to treatments and medications provided for healthcare consumers 120 by healthcare providers 140. Claim information 160G may include information about specific treatments and medications and what is and is not covered by the healthcare consumer's health plan. This information may include specific monetary amounts related to specific treatments and medications. Patient healthcare bill information 160F may include information about amounts a healthcare consumer 120 is charged for healthcare. This information may include specific monetary amounts charged to a healthcare consumer 120 for treatments and medications not covered under the healthcare consumer's health plan. Medication information 160E may include information about medications given to a healthcare consumer 120 before, during and after a treatment.

In one example, a healthcare consumer 120 may go to a doctor because of a broken ankle. The doctor may X-Ray the ankle, put a cast on the ankle and prescribe pain medication. In this example, the healthcare consumer's insurance company may pay 80% of the bill and the healthcare consumer 120 may pay the remaining 20%. The healthcare provider 140, health plan provider 130 and healthcare consumer 120 may use a healthcare management application 180 to manage all of the information related to the healthcare consumer's health condition and network-based service 150 may collect healthcare information data 160 related to the health condition. Information about the physician (e.g., orthopedic specialist) may be maintained in healthcare provider 160D. Information about the orthopedic injury (e.g., broken ankle) may be kept in treatment information 160B. Information about the healthcare consumer's broken ankle may be kept in health condition information 160A, including the date and time of the doctor's visit, the doctor visited and the diagnosis. Treatment information 160B may include information about applying a cast on the ankle and the X-Ray. Medication information 160E may include information about the pain medication prescribed. Health plan information 160C may include information about the healthcare consumer insurance coverage (e.g., co-pay information, percentages covered, etc.). Healthcare consumer 120 healthcare bills 160F may include information about the 20% the healthcare consumer 120 paid for the X-Ray, cast and medication. Healthcare consumer healthcare claims 160G may include claim information regarding monetary amounts covered by the insurance company.

Information collected for healthcare information data 160 may include date and/or time information associated with each data element generated along the health history data stream 240. Network-based service 150 may access healthcare information data 160 so that data may be returned according to a particular date range. As data is collected for healthcare consumers 120 over time, the healthcare consumer's health healthcare information data 160 may include multiple health conditions. In some cases, network-based service 160 may be configured to return results for a specific health condition. In other cases, network-based service 160 may be configured to return results for a specified date range.

Geographic information may be recorded in healthcare information data 160. For example, the zip code of the healthcare consumer 120, the zip code of the healthcare provider 130, the zip code of the facility where the procedure 260 was performed and the zip code of the pharmacy where medication 270 was dispensed. Network-based service 150 may use geographic information when accessing healthcare information data 160 so that results may be returned for specific geographic areas.

Healthcare information data 160 may be related using keys and identification fields, such as healthcare consumer 120 identification numbers and procedure codes. Similarly, healthcare provider information 179 may be linked or related to healthcare consumers 120 using related keys or fields, such as a healthcare provider identification number. Network-based service 150 may use these related fields to join or match data when accessing data. Network-based service 150 or healthcare management application 180 may arrange data in healthcare information 160 in order to optimize queries for analysis purposes. In one example, data may be arranged by geographic region (e.g., separate data tables may be arranged for specific major metropolitan areas). In another example, data may be arranged by common health episodes (e.g., heart disease or cancer). Network-based service 150 and/or healthcare management application 180 may periodically re-arrange data within healthcare management data 160 in order to optimize queries and increase query and/or analysis performance.

In some embodiments, healthcare information data 160 collected by network-based service 150 may be formatted according to a standard exchange format, for example extensible markup language (XML). The network-based service 150 may maintain the healthcare information data 160 in one or more databases or in another suitable format. Healthcare information data 160 may be stored in local or remote storage or in a combination of the two. For example, a database located on a database server accessible by network-based service 150 may be configured to securely store healthcare information data 160 for multiple individual healthcare consumers 120 or for employees of one or more corporations subscribing to a healthcare management service. A database may be stored locally on a healthcare consumer's computing system and may include only his or her personal healthcare information. Network-based service 150 may be configured to collect information from the local computing system.

Figure 3:
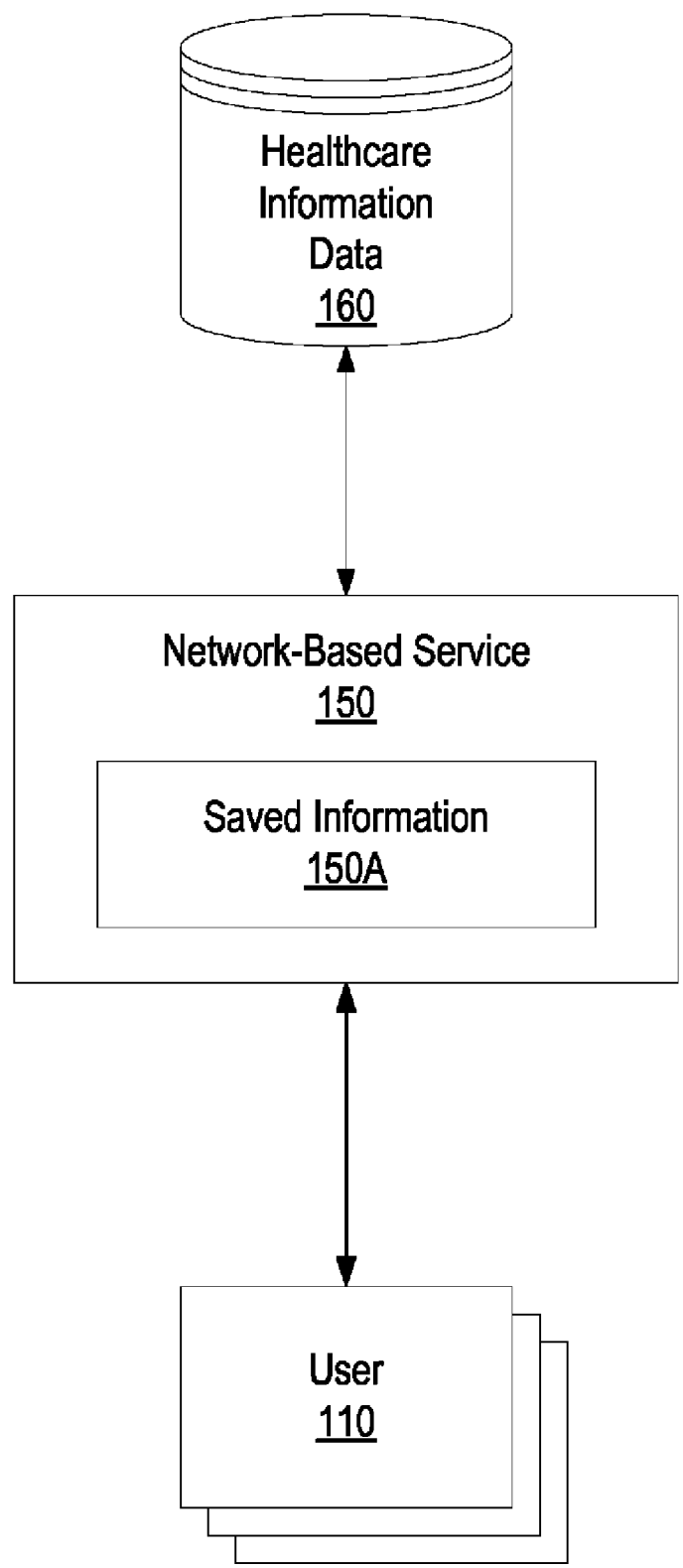
FIG. 3 is a block diagram illustrating a network-based service, according to an embodiment.

FIG. 3 is a block diagram illustrating a network-based service 150, according to an embodiment. Network-based service 150 may be configured to receive a cost estimate request from a user 110 for a specified health episode. In some embodiments, network-based service 150 may receive the cost estimate request directly from user 110 and in other embodiments, network-based service 150 may receive the cost estimate request indirectly through healthcare application 180, or indirectly from another source.

User 110 may be configured as a web application and may be configured to send the request using a web based protocol, such as HTTP. (For more information regarding user 110, see the description below for FIGS. 5-8.) Network-based service 150 may be configured to generate a response to the cost estimate request in a format that can be viewed within a web browser, such as Internet Explorer™ or FireFox™.

Network-based service 150 may access healthcare information data 160 to determine information about a specified health episode. In some embodiments, healthcare information data 160 may be implemented as a relational database, such as Oracle™ or SQL Server™, or another type of database. Network-based service 150 may be configured to format queries related to healthcare information, such as treatment information using a query language such as Structure Query Language (e.g., ANSI SQL, Transact SQL or PL SQL) or another type of query language. Network-based service 150 may format the query to search for specific by matching on certain fields or keys. Network-based service 150 may connect to healthcare information data 160, execute queries against healthcare information data 160 and receive return results.

Network-based service 150 may be configured to generate queries against healthcare information data 160 to determine a plurality of treatment items for a specified health episode. A treatment item may be defined as a specific treatment line item charge for treatment administered to a healthcare consumer 120 by a healthcare provider 140 during a matching health episode. Treatment item may include one or more of: (1) A description of the treatment item, (2) The cost of the treatment item, (3) The date and time the treatment item was administered, (3) The healthcare provider 140 that administered the treatment item, (4) The amount charged by the healthcare provider for the treatment item, (5) The in-network amount charged to the healthcare consumer 120, and/or (6) The out-of-network amount charged to the healthcare consumer 120. Examples of treatment items include medical procedures, medications, office visits, surgical procedures, consultations and tests. Other treatment items have been contemplated. Any treatment line item charge can be referred to as a treatment item. In various embodiments, one or more treatment items are related to a health episode.

In some embodiments, network-based service 150 may be configured to determine cost information for each determined treatment item related to the health episode. Healthcare information data 160 may be arranged in such a way that treatment item data is related to corresponding cost data. When network-based service 150 queries healthcare information 160, the treatment item data may be joined with the related cost data and returned. Network-based service 150 may be configured to generate a response to the cost estimate request wherein the response indicates the plurality of treatment items determined for the specified episode and associated cost information for each determined treatment item. Network-based service 150 may be configured to send the response to the user 110.

A cost estimate request may further comprise insurance plan information. In some embodiments, if the user is not a subscriber to the healthcare management system, the user may submit insurance plan information with the cost estimate request (e.g., by using a user interface similar to the one illustrated in FIG. 5). In other embodiments, if the user is a subscriber to the healthcare management system, the user's insurance plan information may be stored in healthcare information 160 and network-based service 150 may utilize the health plan information when determining cost information. Network-based service 150 may be configured to determine treatment item cost information according to the insurance plan of the user. For example, with the user's insurance plan information, network-based service 150 may generate the response to the user such that each treatment item cost is calculated according to the user's health plan. In some embodiments, if the treatment item is covered under a health plan, the total cost, the amount covered by the health plan and the amount charged to the healthcare consumer 120 (if any) may all be returned to the user.

In some embodiments, healthcare comparative cost information regarding treatment items for a health episode may be returned to the user 110. For example, user 110 may submit a cost estimate request to network-based service 150 for a specific health condition. Network-based service 150 may generate a response for the user that compares two different healthcare providers 140 that treat the same specified health condition. The user 110 may compare the two healthcare provider responses. Network-based service 150 may generate cost comparative information that compares in-network costs to out-of-network costs for each treatment item included in a health episode. The in-network and out-of-network comparative information may be returned to the user 110.

In some embodiments, network-based service 150 may save healthcare provider comparative cost information in saved information 150A, and subsequently, retrieve and send the saved healthcare provider comparative cost information to the user 110 at the user's request. In some cases, network-based service 150 may save in-network and out-of-network comparative cost information in saved information 150A and subsequently, retrieve and send the saved information to the user 110 at the user's request.

In some embodiments, when a response is generated by network-based service 150 for a user 110, the response may be generated so that the healthcare consumers remain anonymous. For example, if a user requests a cost estimate for a specified health episode, the response generated by network-based service 150 may include data for one or more healthcare consumers 120 that recently experienced the same health episode. Although the healthcare consumers' 120 treatment item history and cost history may be returned by network-based service 150, all identifying information may be removed so that the healthcare consumers 120 remain anonymous.

In some embodiments, network-based service 150 may be configured to receive an indication from user 110 specifying a geographic area. In other embodiments, if the user is a subscriber to the healthcare management system, network-based service may retrieve the user's geographic location. Network-based service 150 may be configured to generate a response to user 110 that only includes treatment items originating from healthcare provider sources 140 located within the geographic area. For example, a user 110 may submit an indication to network-based service 150 indicating only healthcare providers 140 within a specific zip code are returned. In some embodiments, network-based service 150 may be configured to only include treatment items originating within the specified zip code. In other embodiments, the geographic area may be specified by area codes. Other geographic indicators have been contemplated.

Network-based service 150 may be implemented by any suitable technique for providing computational functionality. Functional components may be implemented as program instructions that may be stored via a computer-accessible storage medium and executed by one or more processors. In some embodiments, all or portions of network-based service 150 may be implemented by dedicated hardware devices as hardwired or embedded computing functionality. Network-based service 150 may be implemented as a standalone program or process capable of executing within an operating system (such as Microsoft Windows™, Apple Macintosh™ OS, Linux, or Unix (or other operating system environments) independent of other applications, programs or processes. For example, network-based service 150 may be implemented in a programming language such as C or C++ and compiled into an executable code module, or implemented in a scripting language that may be interpreted at application runtime. In another embodiment, network-based service 150 may be implemented as a component of healthcare management application 180. In various embodiments, network-based service 150 may interact with users 110, healthcare management application 180, and healthcare information data 160 via a network 170. In various embodiments network 170 may correspond to the public Internet, a private network internal to an enterprise (e.g., an intranet) or a combination of the two. Network-based service 150 may be implemented in whole or in part with technologies such as Hypertext Markup Language (HTML), Java, Javascript, Perl, Common Gateway Interface (CGI), web service technologies such as .NET™, J2EE, eXtensible Markup Language (XML), Simple Object Access Protocol (SOAP), or other suitable technologies for providing application functionality to users via network 170.

Figure 4:
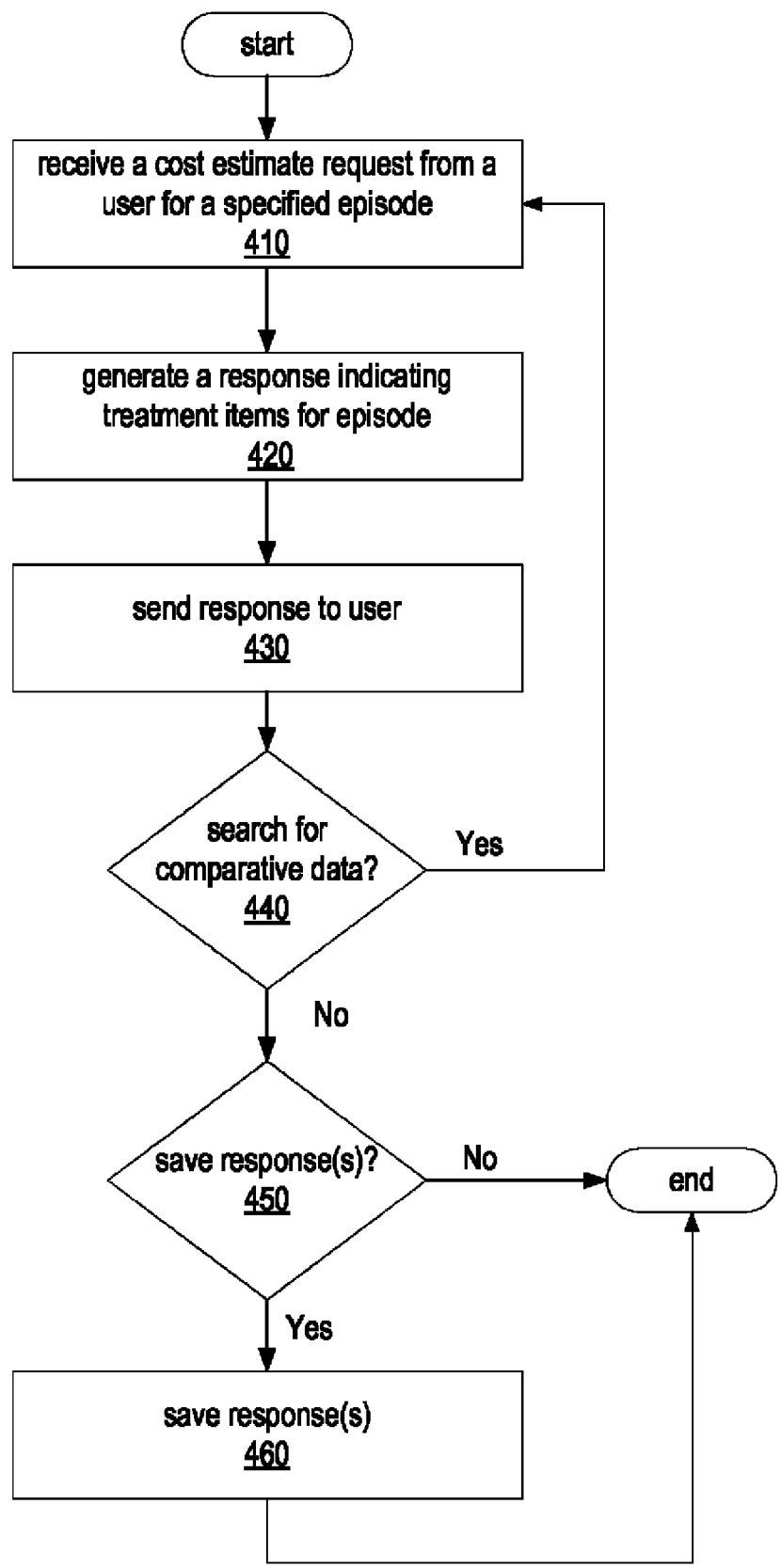
FIG. 4 is a flow diagram illustrating a method for estimating healthcare treatment information for a health condition, according to an embodiment.

FIG. 4 is a flow diagram illustrating a method for estimating healthcare treatment information for a health episode, according to an embodiment. As shown in block 410, network-based service 150 may receive a cost estimate request from a user for a specified health episode. In some embodiments, network-based service 150 may receive the request directly from user 110. In other embodiments, network-based service 150 may receive the request indirectly (e.g., from healthcare management application 180). In some embodiments, the request may specify a geographic area as indicated by a zip code or an area code.

As shown in block 420, network-based service 150 may access healthcare information data 160 to determine a plurality of treatment items for the specified health episode and may also determine cost information for each determined treatment item. Network-based service 150 may generate a response based on data (e.g., from one or more healthcare consumers 120, healthcare providers 140 and health plan providers 130) in healthcare information data 160. Network-based service 150 is configured to determine the plurality of treatment items for the specified health episode in such a way as to keep the healthcare consumers anonymous. In various embodiments, no healthcare consumer personal identifying data may be included in the response.

In some embodiments the response may only include treatment items administered within a specified geographic area.

As shown in block 430, network-based service 150 may send a response to user 110. The response sent to user 110 may include one or more treatment items for the specified health episode. In some embodiments, each treatment item may include a treatment cost, a treatment description, an in-network cost, and an out-of-network cost and a quantity, indicating the number treatment line items administered during a health episode (e.g., two or more blood tests may be administered during the course of a health episode). In some embodiments, in addition to including each treatment item associated with the health episode, the response may also include summary information formatted to show the total in-network cost and the total out-of-network cost a healthcare consumer 120 can expect to pay for the entire health episode.

As shown in block 440, user 110 may be given the option of searching for comparative data, or the initial request may have specified to include comparative data. In some cases two or more healthcare providers may charge different amounts for treating the same health episode. For example, two physicians may charge different amounts to treat the same health condition. In another example, two healthcare facilities (e.g., hospitals) may charge different amounts for similar services. User 110 may be given the option of tailoring the response from network-based service 150 such that two or more healthcare providers are compared. If user 110 chooses to search for comparative data, the flow returns to block 410. If the user 110 chooses not to search for comparative data, the flow proceeds to block 450.

As shown in block 450, user 110 may be given the option of storing network-based service 150 responses. If user 110 chooses to save the generated response, network-based service 150 saves the response as shown in block 460. In some embodiments, user 110 may have several responses for comparative purposes and user 110 may save the comparison information as well. Subsequently, network-based service 150 may be configured to retrieve and send previously saved responses to user 110 at the request of user 110.

Following is one example of the flow depicted in FIG. 4. In this example, as shown in block 410, user 110 (e.g., patient) with an ankle injury, suspecting the ankle injury might be a broken, submits a request to network-based service 150 (e.g., indicating a health episode of broken ankle) In this example, the submitted request includes a zip code of "77777". As shown in block 420, network-based service 150 may access healthcare information data 160 to determine a plurality of treatment items for the specified health episode (e.g., broken ankle) In this example, network-based service determines five doctors within zip code "77777" treat broken ankles Network-based service 150 also determines one or more treatment items for diagnosis, treatment and follow-up care related to broken ankles. Each of the treatment items includes a description, cost, in-network cost estimation and out-of-network cost estimation. As shown in block 430, a response is sent to user 110. In this example, user 110 may display the response within a web browser. The patient sees a list of the five physicians in the patient's area code that treat broken ankles and the patient selects one that the user knows is in her health plan network. The patient sees that in order to diagnose a broken ankle, physicians typically X-Ray the ankle. The in-network cost is $30. In this example, the patient also sees that a cast is typically applied to a broken ankle and the in-network cost is typically $20. The patient also sees that typically five sessions of physical therapy are required at a co-pay cost of $20 a visit for an in-network physical therapist and $40 for out-of-network physical therapist. In this example, the patient chooses not to search for comparative data (block 440) but chooses to save the response (block 460) in order to view it again at a later date. In this example, the patient was able to view individual treatment items typical for broken ankles and was also able to get a cost estimate for the entire health episode.

Although the above example is described for a healthcare embodiment, other embodiments of the system may include any situation where a consumer interacts with a service provider and/or insurer. For example, a consumer may have automobile insurance and the consumer may experience an automobile accident. The consumer may visit a body shop to receive an auto repair estimate. In this example, a consumer may submit a request to the network-based service indicating a damaged right front quarter-panel on a 2007 Toyota Corolla as the specified episode. The network-based service may access data 160 (e.g., implemented to store data for previously collected auto repairs/claims) to determine a list of service items indicating labor costs and all associated part costs required to repair the damage. In this example, the network-base service may determine the consumer's auto insurance deductible information and determine the estimated amount the consumer may pay to repair the automobile.

In various other embodiments, the system described herein may be implemented for consumers of home owners insurance, for consumers of veterinarian (e.g., pet healthcare) services and for home remodeling services. Many other implementations have been contemplated. In general, embodiments are not limited to healthcare, but may apply to any situation in which consumers experience an episode and receive corresponding service items (e.g., service actions and/or products). The system may collect data about such previous episodes from multiple sources (e.g., consumers, providers, insurers, etc.). In response to a user request specifying an episode, the data may be analyzed to determine typical service items performed for such an episode and associated costs. A response may be generated indicating the items and costs (e.g., in a line item format) for the specified episode.

FIGS. 5 through 8 illustrate a user interface that may be provided by network-based service 150. The figures illustrate how a user interface may be utilized to submit a cost estimate request to network-based service 150 and display results returned from network-based service 150, according to an embodiment. The screen illustrations depicted in FIGS. 5-8 are for illustration purposes. Actual embodiments may differ.

Figure 5:
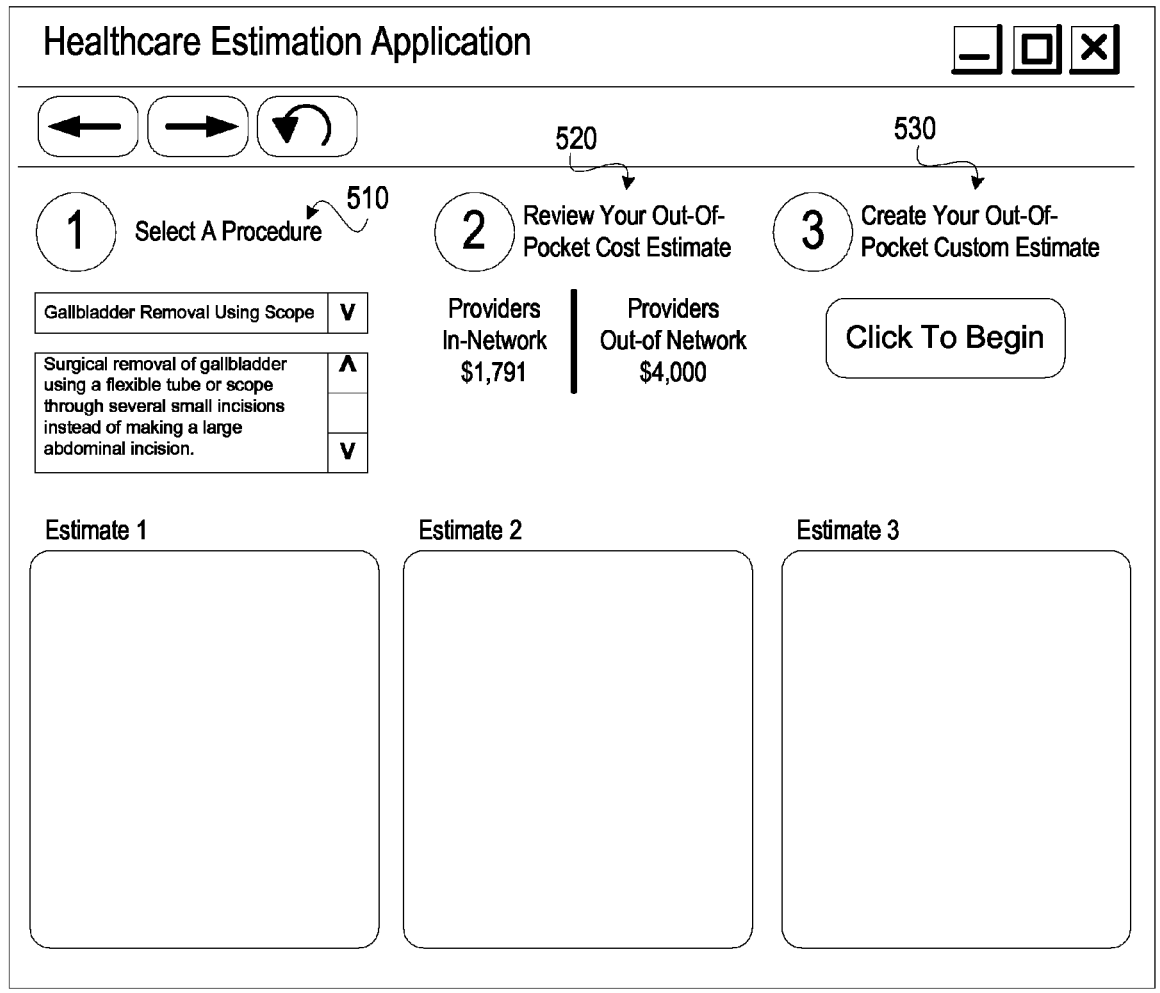
FIG. 5 is a user interface diagram, illustrating the selection of a health episode within a healthcare estimation application, according to an embodiment.

FIG. 5 is a user interface diagram, illustrating the selection of a procedure (e.g., a health condition associated with a health episode) within a healthcare estimation application, according to an embodiment. As shown at item 510, the first step is to select a procedure to associate with the cost estimate request. In the illustrated example, the selection, "Gallbladder removal using a scope" is chosen from a list of many possible selection possibilities. A brief description of the gallbladder procedure is provided under the procedure title.

As shown at item 520, the network-based service 150 may provide the healthcare estimation application with an out-of-pocket summary cost estimation associated with the selected procedure. In this example, the out-of-pocket cost estimate is for the entire health episode, "Gallbladder removal using a scope". The in-network estimate is $1,791 and the out-of-network estimation is $4,000. As shown at item 530, the user may press the button, "Click To Begin" to continue with the health cost estimate process.

FIG. 6 is a screen diagram illustrating the display of treatment options and treatment item costs associated with the procedure selected (as shown in FIG. 5). In some embodiments, network-based service 150 may receive selection criteria from the user. The selection criteria may comprise selected treatment items to include or exclude in the cost estimate. Further, the selection criteria may allow the user to change healthcare professionals for selected treatment items or select in-network or out-of-network treatment items associated with the health episode. The network-based service may generate the cost estimate response according to the selection criteria. Note that in this example, the healthcare estimation application submits a request to network-based service 150 and network-based service returns the treatment item information, including treatment descriptions and amounts, which may be displayed as shown in FIG. 6.

At item 610, individual treatment items may be displayed related to a diagnosis (e.g., Gallbladder removal using a scope. In this example, the tissue test and chest X-Ray are individual treatment items typically associated with the selected procedure. (Other procedures may have other diagnosis treatment items.) In this example, if the user selects an "In Network Lab" the out-of-pocket estimate is $78 and the In-Network amount saved is $0. The Chest X-Ray out-of-pocket estimate is $4 for an in-network facility. Similar treatment items are shown at item 620 for treatments and procedures (e.g., anesthesiologist and surgeon) as well as follow-up care at item 630. In this example, the healthcare estimation application allows a human user (utilizing the healthcare estimation application) to tailor the application by selecting different in-network and out-of-network providers. The amounts displayed for each treatment item (e.g., out-of-pocket estimate and in-network savings) may change dependent upon the provider(s) selected. For example, at item 620, the user may select a different surgeon and the healthcare estimation application may determine a different out-of-pocket estimate dependent on the selected surgeon. Item 640 provides a summary of all out-of-pocket costs dependent upon the choices selected for each treatment item. In this example, the total out-of-pocket estimate is $2,852. Item 650 shows the total estimated amount paid by the user's health plan as $4,152 and the estimated amount billed by the provider(s) is $7,004. Note that the network-based service 150 has returned individual treatment item costs and descriptions as well as aggregate amounts associated with the selected procedure.

Figure 7:
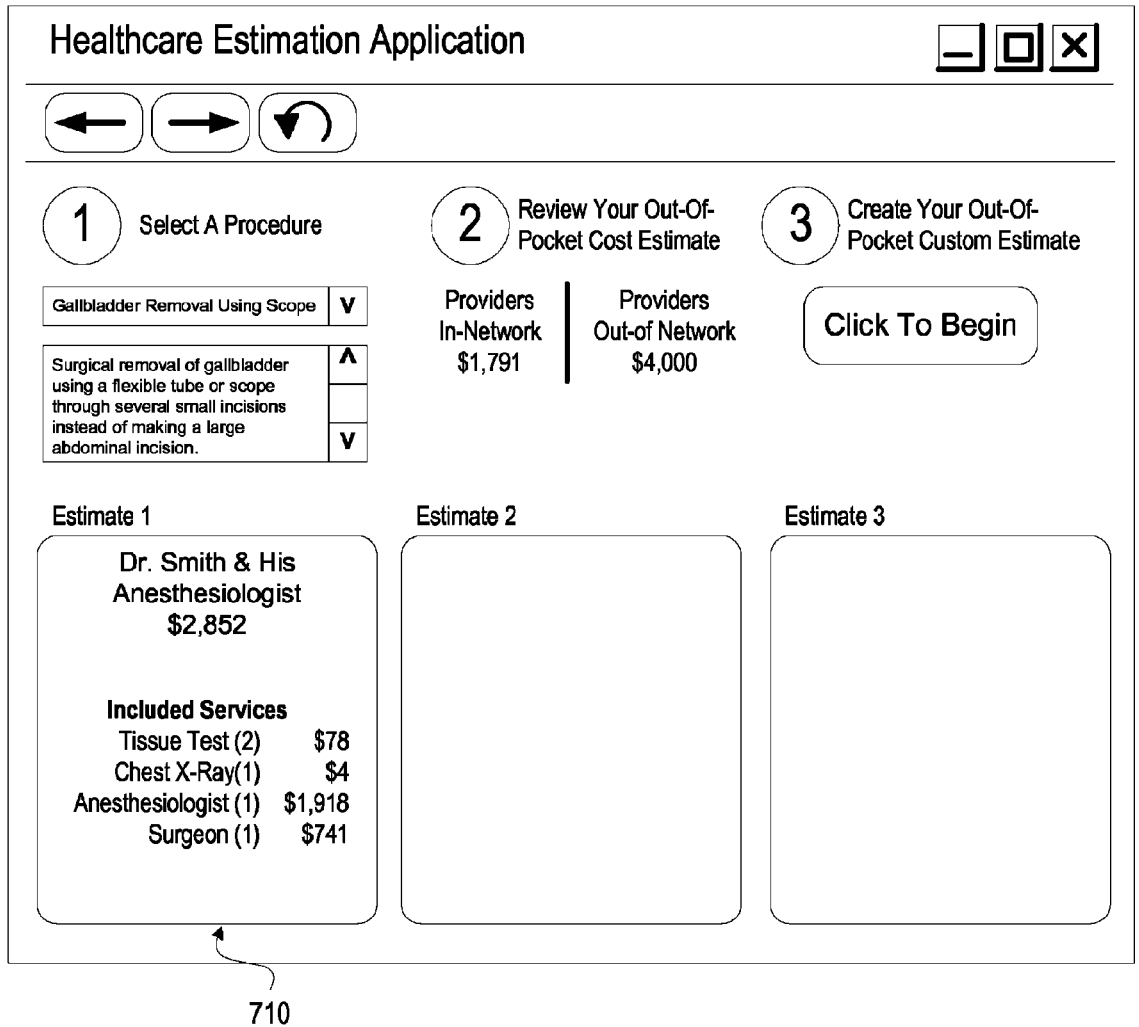
FIG. 7 is a user interface diagram, illustrating the display of summary information related to one treatment scenario, according to an embodiment.

FIG. 7 is a user interface diagram, illustrating the display of summary information related to one treatment scenario, according to an embodiment. In this illustration the user has saved a summary (item 910) of the selections chosen in the previous screen (e.g., FIG. 6). At this point, the user may create another estimate using different selection criteria for comparison purposes.

Figure 8:
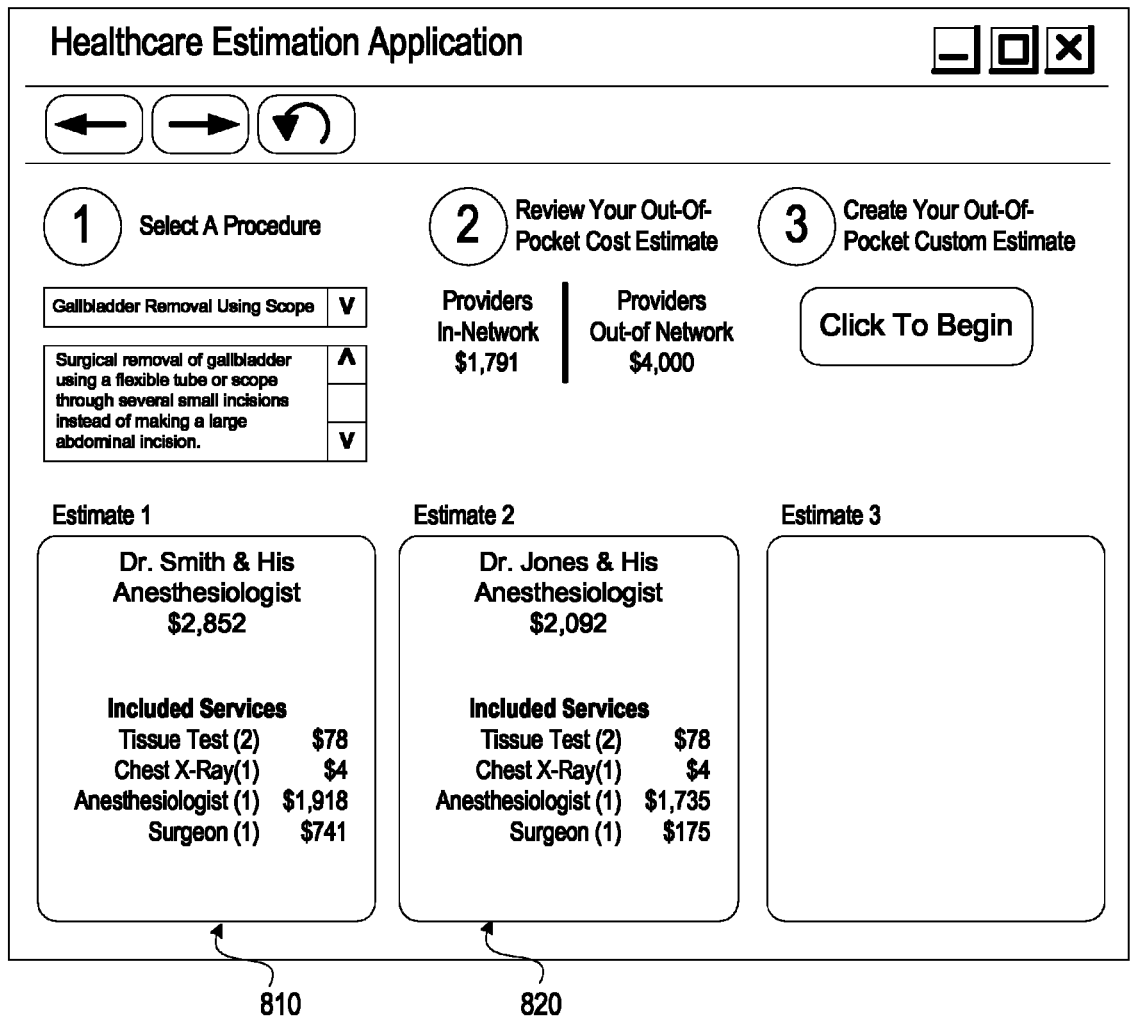
FIG. 8 is a user interface diagram, illustrating the display of summary information related to two comparative treatment scenarios, according to an embodiment.

FIG. 8 is a user interface diagram, illustrating the display of summary information related to two comparative treatment scenarios, according to an embodiment. The first treatment scenario (Item 810) is for Dr. Smith and his anesthesiologist; the estimated amount the patient would pay is $2,852. The second treatment scenario (Item 820) is for Dr. Jones and his anesthesiologist; the estimated amount the patient would pay is $2,092. Note that network-based service 150 has returned treatment information to the healthcare estimation application that allows the human user to compare data dependent on the treatment selections. In some embodiments, network-based service 150 may save the cost comparison information, the in-network and out-of-network comparative cost information (e.g., Estimates 1 and 2 as shown at items 810 and 820), and subsequently, network-based service 150 may retrieve and send the information to the healthcare estimation application so that the user may view the data at a later time.

Figure 9:
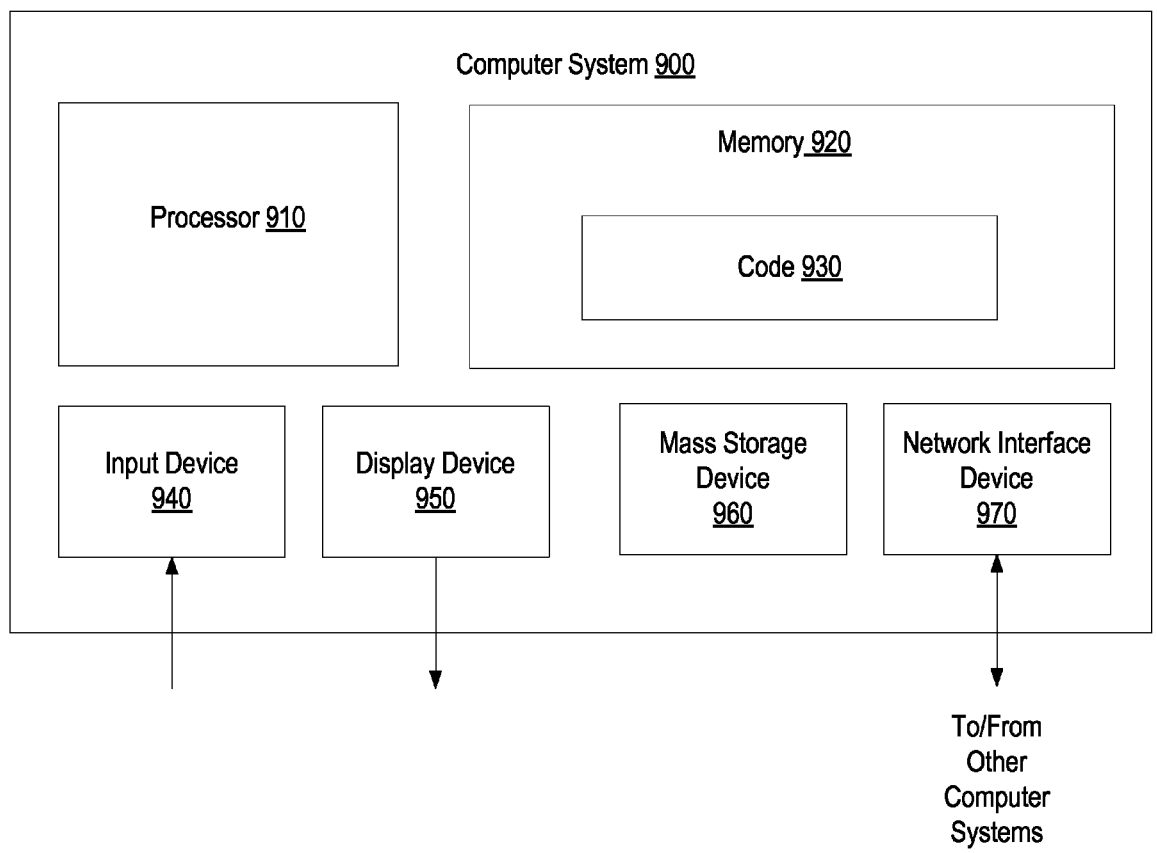
FIG. 9 is a block diagram, illustrating a system for implementing a network-based service, according to an embodiment.

FIG. 9 is a block diagram illustrating a computing device, according to an embodiment. Various components of embodiments of the network-based service 150, healthcare management application 180, user 110, health plan providers 130, healthcare providers 140 and healthcare consumers 120, as described herein, may be executed on one or more computer systems, which may interact with various other devices. One such computer system is illustrated by FIG. 9. In the illustrated embodiment, computer system 900 includes one or more processors 910 coupled to a system memory 920. Computer system 900 further includes a network interface 970 and one or more input/output devices 940/950, such as a cursor control device, keyboard, audio device and display device 950. In some embodiments, it is contemplated that embodiments may be implemented using a single instance of computer system 900, while in other embodiments multiple such systems, or multiple nodes making up computer system 900, may be configured to host different portions or instances of embodiments. For example, in one embodiment some elements may be implemented via one or more nodes of computer system 900 that are distinct from those nodes implementing other elements.

In various embodiments, computer system 900 may be a single processor system including one processor 910, or a multiprocessor system including several processors 910 (e.g., two, four, eight, or another suitable number). Processors 910 may be any suitable processor capable of executing instructions. For example, in various embodiments, processors 910 may be general-purpose or embedded processors implementing any of a variety of instruction set architectures (ISAs), such as the x86, PowerPC, Scalable Processor Architecture (SPARC), or Million Instructions per Second (MIPS) Instruction Set Architectures (ISAs), or any other suitable ISA. In multiprocessor systems, each of processors 910 may commonly, but not necessarily, implement the same ISA.

System memory 920 may be configured to store program instructions 930 and/or data accessible by processor 910. In various embodiments, system memory 920 may be implemented using any suitable memory technology, such as static random access memory (SRAM), synchronous dynamic RAM (SDRAM), nonvolatile/Flash-type memory, or any other type of memory. Program instructions and/or data may also be stored, for example, on a hard disk. In the illustrated embodiment, program instructions and data implementing desired functions, such as those described above for the network-based service 150, are shown stored within system memory 920 as program instructions 930 and data storage 960, respectively. In other embodiments, program instructions and/or data may be received, sent or stored upon different types of computer-accessible media or on similar media separate from system memory 920 or computer system 900. Generally speaking, a computer-accessible medium may include storage media or memory media such as magnetic or optical media, e.g., disk or Digital Versatile Disc (DVD) Read Only Memory (ROM)/Compact Disk-Read Only Memory (CD-ROM) coupled to computer system 900. Program instructions and data stored via a computer-accessible medium may be transmitted by transmission media or signals such as electrical, electromagnetic, or digital signals, which may be provided via a communication medium such as a network and/or a wireless link, such as may be implemented via network interface 970.

Network interface 970 may be configured to allow data to be exchanged between computer system 900 and other devices attached to a network, such as other computer systems, or between nodes of computer system 900. In various embodiments, network interface 970 may support communication via wired or wireless general data networks, such as any suitable type of Ethernet network, for example; via telecommunications/telephony networks such as analog voice networks or digital fiber communications networks; via storage area networks such as Fibre Channel Storage Area Networks (SANs), or via any other suitable type of network and/or protocol.

Input/output devices 940 and 950 respectively, may in some embodiments include one or more display terminals, keyboards, keypads, touchpads, scanning devices, voice or optical recognition devices, or any other devices suitable for entering or retrieving data by one or more computer system 900. Multiple input/output devices 940 and 950 may be present in computer system 900 or may be distributed on various nodes of computer system 900. In some embodiments, similar input/output devices may be separate from computer system 900 and may interact with one or more nodes of computer system 900 through a wired or wireless connection, such as over network interface 970.

Memory 920 may include program instructions 930, configured to implement at least a portion of embodiments of the network-based service 150 as described herein, and data storage 960, comprising various documents, tables, databases, etc. accessible by program instructions 930. In one embodiment, program instructions 930 may include software elements of the network-based service 150 illustrated in the Figures, and data storage 960 may include data used in embodiments of the network-based service 150. In other embodiments, different software elements and data may be included. Program instructions and/or data may be stored, for example, on various types of memory including hard disks.

Those skilled in the art will appreciate that computer system 900 is merely illustrative and is not intended to limit the scope of the network-based service 150 as described herein. In particular, the computer system and devices may include any combination of hardware or software that can perform the indicated functions, including computers, network devices, internet appliances, PDAs, mobile phones, pagers, etc. Computer system 900 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 900 may be transmitted to computer system 900 via transmission media or signals such as electrical, electromagnetic, or digital signals, provided via a communication medium such as a network and/or a wireless link. Various embodiments may further include receiving, sending or storing instructions and/or data implemented in accordance with the foregoing description upon a computer-accessible medium. Accordingly, the present invention may be practiced with other computer system configurations.

Various embodiments may further include receiving, sending or storing instructions and/or data implemented in accordance with the foregoing description upon a computer-accessible medium. Generally speaking, a computer-accessible medium may include storage media or memory media such as magnetic or optical media, e.g., disk or DVD/CD-ROM, volatile or non-volatile media such as RAM (e.g. Synchronous Dynamic RAM (SDRAM), Double Data Rate RAM (DDR RAM), RAMBUS Dynamic RAM (RDRAM), Static RAM (SRAM), etc.), Read Only Memory (ROM), etc. as well as transmission media or signals such as electrical, electromagnetic, or digital signals, provided via a communication medium such as network and/or a wireless link.

The various methods as illustrated in the Figures and described herein represent exemplary embodiments of methods. The methods may be implemented in software, hardware, or a combination thereof. The order of method may be changed, and various elements may be added, reordered, combined, omitted, modified, etc.

Various modifications and changes may be made as would be obvious to a person skilled in the art having the benefit of this disclosure. It is intended that the invention embrace all such modifications and changes and, accordingly, the above description to be regarded in an illustrative rather than a restrictive sense.

What is claimed is:

1. A system, comprising: one or more processors; and
memory coupled to the one or more processors, and storing program instructions executable by the one or more processors to implement a system configured to:
collect, from a plurality of sources, historical healthcare data about actual healthcare episodes previously experienced by respective ones of a plurality of consumers other than a user of the system, each episode having one or more service items associated with diagnosis, treatment, and followup related to the episode, the one or more service items including one or more of treatments and medication related to the episode, actual historical cost data associated with the one or more service items, and provider information indicating at least one provider who performed the service item;
receive a cost estimate request for a specified episode, the request being received from the user not of the plurality of consumers;
receive input from the user selecting at least two service providers to compare;
in response to receiving the cost estimate request: access the historical healthcare data;
analyze the historical healthcare data to determine service items previously accomplished by the at least two user-selected service providers, for at least one of the plurality of consumers for the specified episode, and to determine actual historical cost information for each determined service item, for the at least two user-selected service providers according to the historical healthcare data; and
generate a response to the cost estimate request which includes a comparison of the actual historical costs of service items previously accomplished by the at least two user-selected service providers for the specified episode, wherein the response indicates service item information for each determined service item, the service item information including at least an in-network actual cost for each of the at least two user-selected service providers for the service item, an out of network actual cost for each of the at least two user-selected service providers for the service item, the actual historical cost information provided as a cost comparison of the cost of individual ones of each of the plurality of service items at each of the at least two user-selected service providers.

2. A non-transitory computer-accessible storage medium, comprising program instructions, wherein the program instructions are computer-executable to implement a system to:
collect, from a plurality of sources, historical healthcare data about actual healthcare episodes previously experienced by respective ones of a plurality of consumers other than a user of the system, each episode having one or more service items associated with diagnosis, treatment, and followup related to the episode, the one or more service items including one or more of treatments and medication related to the episode, actual historical cost data associated with the one or more service items, and provider information indicating at least one provider who performed the service item;
receive a cost estimate request for a specified episode, the request being received from the user not of the plurality of consumers;
receive input from the user selecting at least two service providers to compare;
in response to receiving the cost estimate request: access the historical healthcare data;
analyze the historical healthcare data to determine service items previously accomplished by the at least two user-selected service providers, for at least one of the plurality of consumers for the specified episode, and to determine actual historical cost information for each determined service item, for the at least two user-selected service providers according to the historical healthcare data; and
generate a response to the cost estimate request which includes a comparison of the actual historical costs of service items previously accomplished by the at least two user-selected service providers for the specified episode, wherein the response indicates service item information for each determined service item, the service item information including at least an in-network actual cost for each of the at least two user-selected service providers for the service item, an out of network actual cost for each of the at least two user-selected service providers for the service item, the actual historical cost information provided as a cost comparison of the cost of individual ones of each of the plurality of service items at each of the at least two user-selected service providers.

3. The system as recited in claim 1, wherein to generate the response the system is further configured to:
analyze insurance plan information of the user; and adjust the associated cost information for each determined service item in the response according to the user's insurance plan information.

4. The system as recited in claim 1, wherein said historical healthcare data comprises healthcare information, wherein said collecting comprises collecting, from a plurality of types of sources, healthcare information about health episodes each experienced by respective ones of a plurality of healthcare consumers, wherein the types of sources comprise two or more of a health plan provider source, a healthcare provider source, and a healthcare consumer source; and
wherein said plurality of service items comprise a plurality of treatment items.

5. The system as recited in claim 4, wherein to generate the response the system is further configured to:
obtain from the healthcare information, healthcare cost information comprising amounts previously charged by a plurality of healthcare providers for the plurality of treatment items; and
include in the associated cost information, for each determined treatment item in the response, comparative estimated costs for the plurality of healthcare providers.

6. The system as recited in claim 4, wherein to generate the response the system is further configured to:
obtain in-network and out-of-network comparative cost information from the healthcare information; and include in the response a comparison of in-network cost information to the out-of-network cost information for each of the plurality of treatment items determined for the specified episode.

7. The system as recited in claim 1, wherein the network-based service is further configured to:
send the generated response to the user; save a copy of the generated response; and
subsequent to sending the generated response to the user, retrieve the copy of the generated response and send the copy of the generated response to the user in response to a request for the saved copy from the user.

8. The system as recited in claim 1, wherein to access the historical healthcare data the system is further configured to locate previously collected historical healthcare data for the specified episode experienced by ones of the plurality of consumers.

9. The system as recited in claim 8, wherein the system is further configured to generate said response such that personal identifying information of the ones of the plurality of healthcare consumers remains anonymous.

10. The system as recited in claim 1, wherein the system is further configured to:
receive an indication from the user specifying a geographic area;
wherein accessing the data is based on the specified geographic area; and
generate said response such that the associated cost information for each determined service item is specific to the user's geographic area.

11. The computer-accessible storage medium as recited in claim 2, wherein to generate the response the system is further configured to: analyze insurance plan information of the user; and
adjust the associated cost information for each determined service item in the response according to the user's insurance plan information.

12. The computer-accessible storage medium as recited in claim 2, wherein said data comprises healthcare information, wherein said collecting comprises collecting, from a plurality of types of sources, healthcare information about health episodes each experienced by respective ones of a plurality of healthcare consumers, wherein the types of sources comprise two or more of a health plan provider source, a healthcare provider source, and a healthcare consumer source; and wherein said plurality of service items comprise a plurality of treatment items.

13. The computer-accessible storage medium as recited in claim 12, wherein to generate the response the system is further configured to:
obtain, from the healthcare information, healthcare cost information comprising amounts previously charged by a plurality of healthcare providers for the plurality of treatment items; and
include, in the associated cost information for each determined treatment item in the response, comparative estimated costs for the plurality of healthcare providers.

14. The computer-accessible storage medium as recited in claim 12, wherein to generate the response the system is further configured to:
obtain in-network and out-of-network comparative cost information for the user's insurance plan; and
include in the response a comparison of in-network cost information to out-of-network cost information for one or more of the plurality of treatment items determined for the specified episode.

15. The computer-accessible storage medium as recited in claim 2, wherein the system is further configured to:
send the generated response to the user; save a copy of the generated response; and
subsequent to sending the generated response to the user, retrieve the copy of the generated response and send the copy of the generated response to the user in response to a request for the saved copy from the user.

16. The computer-accessible storage medium as recited in claim 2, wherein the system is further configured to generate said response such that personal identifying information of the ones of the plurality of consumers remains anonymous.

17. The computer-accessible storage medium as recited in claim 2, wherein the system is further configured to send the response to a web browser client for the user.

18. The computer-accessible storage medium as recited in claim 2, wherein the system is further configured to:
receive an indication from the user specifying a geographic area;
wherein accessing the data is based on the specified geographic area; and
generate said response such that the associated cost information for each determined service item is specific to the user's geographic area.

* * * * *